(12) United States Patent
LaValley (10) Patent No.: US 7,993,609 B2
(45) Date of Patent: Aug. 9, 2011

(54) PACKAGE FOR CHEMICALS

(75) Inventor: Patrick LaValley, Elk River, MN (US)

(73) Assignee: Sterilucent, Inc., Minneapolis, MN (US)

( * ) Notice: Subject to any disclaimer, the term of this patent is extended or adjusted under 35 U.S.C. 154(b) by 465 days.

(21) Appl. No.: 12/317,894

(22) Filed: Dec. 30, 2008

(65) Prior Publication Data

US 2010/0163448 A1     Jul. 1, 2010

(51) Int. Cl.
*B01L 3/00*     (2006.01)

(52) U.S. Cl. ............... 422/547; 422/2; 422/28; 422/40; 422/41; 422/292; 422/300; 422/305; 422/33; 422/400; 422/502; 422/570; 435/1.1; 435/287.7; 435/288.1; 435/288.3; 435/294.1; 435/297.1; 435/297.5; 435/304.3; 435/31; 435/325; 220/200; 220/203.11; 220/203.13; 220/256.1; 220/259.4; 220/288; 220/315; 220/371; 206/222; 206/438; 206/459.1; 206/484; 206/524.3; 206/524.4; 206/524.5

(58) Field of Classification Search ............... 422/2, 28, 422/29, 40, 41, 292, 300, 305, 33, 400, 502, 422/547, 570; 435/1.1, 287.7, 288.1, 288.3, 435/294.1, 297.1, 297.5, 304.3, 31, 325; 206/222, 438, 459.1, 484, 524.3, 524.4, 524.5; 220/83, 189.06, 207, 566

See application file for complete search history.

(56) References Cited

U.S. PATENT DOCUMENTS

| | | | |
|---|---|---|---|
| 4,061,455 A | 12/1977 | von Holdt | |
| 4,109,818 A | 8/1978 | Hascoe et al. | |
| 4,635,661 A | 1/1987 | Uematsu et al. | |
| 4,817,800 A | 4/1989 | Williams et al. | |
| 4,869,286 A | 9/1989 | Williams et al. | |
| 4,899,519 A | 2/1990 | Williams et al. | |
| 4,909,287 A | 3/1990 | Williams et al. | |
| 4,913,196 A | 4/1990 | Williams et al. | |
| 4,941,518 A | 7/1990 | Williams et al. | |
| 5,692,634 A | 12/1997 | Jenkins et al. | |
| 5,882,611 A | 3/1999 | Williams et al. | |
| 5,887,716 A | 3/1999 | Williams et al. | |
| 6,196,409 B1 | 3/2001 | Lake et al. | |
| 6,296,802 B1 | 10/2001 | Blazaitis et al. | |
| 6,495,100 B1 * | 12/2002 | Lin et al. | 422/29 |
| 6,691,704 B2 | 2/2004 | Bibi et al. | |
| 6,730,510 B2 * | 5/2004 | Roos et al. | 435/288.3 |
| 6,827,232 B1 | 12/2004 | Hara et al. | |
| 7,037,455 B2 | 5/2006 | Marine | |
| 7,074,374 B1 | 7/2006 | Fujii et al. | |
| 7,101,512 B2 | 9/2006 | Hahs et al. | |
| 7,143,903 B2 | 12/2006 | Musaragno | |
| 2003/0200974 A1 | 10/2003 | Shaw et al. | |

(Continued)

FOREIGN PATENT DOCUMENTS

WO     WO 96/11857     4/1996

*Primary Examiner* — Lyle Alexander
*Assistant Examiner* — Dennis M White
(74) *Attorney, Agent, or Firm* — Thomas J. Nikolai; Nikolai & Mersereau, P.A.

(57) ABSTRACT

A container is provided for holding a chemical compound or mixture. Areas are provided on the surface of the container which allow for gaseous by-products from the chemical contained within the container to permeate from a chamber through the surface of the container. A septum is over-molded into the surface of the container. The septum is formed in such a manner that it provides a sealing effect to close an opening in the container.

46 Claims, 9 Drawing Sheets

U.S. PATENT DOCUMENTS

| | | |
|---|---|---|
| 2004/0050744 A1 | 3/2004 | Hama et al. |
| 2004/0140308 A1 | 7/2004 | Maenke |
| 2005/0263421 A1 | 12/2005 | Kohler |
| 2005/0263422 A1 | 12/2005 | Kohler |
| 2006/0096594 A1 | 5/2006 | Bonney et al. |
| 2008/0006634 A1 | 1/2008 | Asao |
| 2008/0079195 A1 | 4/2008 | Chan |

* cited by examiner

PACKAGE FOR CHEMICALS

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. W81XWH-05-1-0398 awarded by USA Medical Research ACQ Activity; Office of Naval Research SBIR Phase II, Contract No. N00014-06-M-0301 and Contract No. 5R44HL074653-03 awarded by National Institute of Health SBIR Phase II.

CROSS-REFERENCED TO RELATED APPLICATIONS

Not applicable

FIELD OF THE INVENTION

The present invention relates to chemical storage containers. More specifically, the present invention relates to unique and novel chemical storage containers that are rupture-resistant, permit gaseous by-products of the stored chemical to permeate, and include a sealed port for extraction of the stored chemical from the container.

BACKGROUND OF THE INVENTION

Various types of containers are employed to store chemicals. The composition of such containers is typically a function of the type of chemical stored and the anticipated use for the chemical.

Various mixtures and compounds are employed in chemical processes. Some are very stable and non-toxic. Others are quite volatile and unstable. Some present little, if any, risk to humans. Others are quite dangerous. Unstable compounds and mixtures can produce by-products, some of which are safe and others are dangerous.

By way of example, hydrogen peroxide is a chemical compound that is highly soluble in water. Various hydrogen peroxide mixtures (i.e., solutions) are employed as a bleach, deodorizing agent, antiseptic, disinfectant, or other purposes. Pure hydrogen peroxide solutions, completely free from contamination, are highly stable. However, trace impurities such as copper, iron, other transition metals and other materials can have a catalytic effect causing the hydrogen peroxide to decompose into water and oxygen.

Oxygen is less soluble in water than hydrogen peroxide. Thus, aqueous solutions of hydrogen peroxide tend to outgas oxygen as the hydrogen peroxide decomposes.

Despite its stability, hydrogen peroxide presents specific hazards. Hydrogen peroxide in high concentrations is a strong oxidizing agent that will react vigorously at ambient temperatures when stored in contact with cellulosic and other organic compounds. It is, therefore, generally recommended that hydrogen peroxide be stored in well ventilated, cool areas. Yet this is not always practical. Concentrated hydrogen peroxide solutions and hydrogen peroxide vapor are corrosive and strongly irritating to humans.

All of these characteristics of hydrogen peroxide must be considered when designing a suitable package for containing this compound. Likewise, the package must be designed to permit the hydrogen peroxide mixture to be extracted safely from the package for use.

In the past, hydrogen peroxide has also been used as a sterilant. Various packages have been employed in the prior art for storing the hydrogen peroxide, shipping the hydrogen peroxide and dispensing the hydrogen peroxide sterilant into a sterilization chamber. Examples of such prior art packages are shown in U.S. Pat. No. 4,817,800 granted Apr. 4, 1989 to Williams et al; U.S. Pat. No. 5,882,611 granted Mar. 16, 1999 to Williams et al; U.S. Patent Application Publication No. 2005/0263422 dated Dec. 1, 2005 and U.S. Pat. No. 7,101,52 granted Sep. 5, 2006 to Hahs et al. Each of these packages comprises a flat, rectangular cassette made of plastic or other suitable material. The cassette includes walls forming a plurality of compartments. Positioned in each compartment is a cell. The cells are formed using two sheets of plastic having mating recesses therein. The peripheries of the recesses are bonded together to form a series of cells held together as a single cell pack in a fashion similar to bubble wrap packaging. The cell pack is then captured between mating portions of the cassette so that each cell is securely gripped in an individual compartment and each compartment is separated from the others. A small, predetermined quantity of the liquid sterilant is contained in each cell. Each compartment has a pair of holes through the plastic walls of the compartment. To extract the sterilant from a cell, a needle is inserted through a lower hole. This needle punctures the cell within the compartment. The sterilant is then extracted through the lower hole in the compartment using pressure which is applied through an upper hole in the compartment to force the sterilant out the cell (and compartment) through the lower hole in the compartment.

Packages of the type described in the above-referenced patents have a number of disadvantages. First, the multi-cell package design contributes to the complexity and expense of the unit used to extract sterilant from the individual cells of the package. Either the needle or the package must be moved to precisely align a hole in a particular compartment with the needle of the extraction device. Only when such precise alignment is achieved can the needle be inserted into the hole, puncture the cell of the compartment and extract the contents. Such alignment is required for each of the compartments of the package. Similar issues arise when filling multiple cells with sterilant.

Second, when the package of the type shown in these prior art patents is employed, the extraction system must employ some logic and control scheme so the system knows which cells have been evacuated and which cells still contain sterilant. The filling system must employ similar logic and control.

Third, the design of the packages shown in the above-referenced patents makes the packages susceptible to improper placement in an extraction device. The outer walls of the container form a rectangle. Yet the structures contained within the rectangle dictate that the package have a top, a bottom, a front and a back. The package is, therefore, susceptible to being inserted in a filling station or an extraction station either upside down, backwards or both, unless special provisions are added to key the cartridge in the station.

Fourth, filling multiple smaller cells with a specific amount of liquid to achieve a total volume of liquid is less accurate than filling one larger cell.

Fifth, the prior art is overly complex requiring both pressure and vacuum sources to remove the contents of a cell.

The small size of the individual cells and compartments presents still other problems. The contents of a single cell are likely insufficient to complete a sterilization cycle. Use of the contents of multiple cells may add to the time required for sterilization. If the contents of all of the cells are not used during a sterilization cycle, the result may be undue waste of the sterilant or disposal problems. If one tries to deal with these problems by using the remaining sterilant in the next sterilization cycle, other problems can arise, particularly if the sterilant remaining in the package is insufficient to complete the next cycle.

Other problems can arise from the size and geometry of the cells of the packages in the prior art patents. The ratio between the volume of sterilant each individual cell contains and the surface area of the plastic forming the cell results in increased chemical and physical interaction between the sterilant and the plastic. When hydrogen peroxide is used as a sterilant, its strong oxidizing characteristics can lead to decomposition of the plastic. Likewise, the plastic can present impurities that catalyze the decomposition of hydrogen peroxide into water and oxygen. The prior art packages do not address the inevitable build-up of oxygen gas in the package. This can occur in different cells at different rates leading either to non-uniform cell failure or non-uniform decomposition of hydrogen peroxide to the point where it can no longer be effectively used as a sterilant.

BRIEF SUMMARY OF THE INVENTION

In view of the foregoing, a first object of the present invention is to provide a durable package that can contain a chemical.

A second object of the present invention is to provide such a package in which the chemical contained is a compound or mixture.

A third object of the present invention is to provide such a package that can safely contain a chemical compound or mixture that has hazardous properties.

A fourth object of the invention is to contain such chemicals and permit such chemicals to be safely and effectively used as a sterilant.

A fifth object of the invention is to provide such a package that is ideally suited to contain and permit hydrogen peroxide to be used as a sterilant.

A sixth object of the invention is to provide a single cell package that safely contains a sufficient quantity of sterilant to complete a sterilization process.

A seventh object of the invention is to provide a package shaped for easy and error-free insertion into a device used to extract the chemical contents of the package.

An eighth object of the invention is to provide a package designed to be mated with the extraction device of a sterilization system.

A ninth object of the invention is to provide a package that provides for the controlled release of gases through permeation resulting from any decomposition of the chemical stored in the packages, thus avoiding the need for venting.

A tenth object of the invention is to provide a package that reduces the rate of decomposition of its contents.

An eleventh object of the invention is to provide a package that allows the user to safely determine whether the package contents have been extracted and used.

A twelfth object of the invention is to provide a package that allows a user to safely determine if the package has leaked.

A thirteenth object of the invention is to provide a package designed to withstand external forces it is likely to be subjected to during shipping and handling even in remote, harsh environments.

A fourteenth object of the invention is to provide a package that can be used in all environments including extremely cold, hot, wet and dry environments.

A fifteenth object of the invention is to provide a package that can be safely transported by sea or by air in either a pressurized or unpressurized environment.

A sixteenth object of the invention is to provide a package that is compact, lightweight and multilayered.

These and other objects are achieved by providing a container comprising a shell and first and second portions that define, surround and encapsulate a chamber in which a chemical is contained. Each portion is integrally molded to include an outer rim surrounding a containing surface, an outwardly projecting wall, and a plurality of strengthening gussets coupled to a containing surface and the wall. The containing surface of each portion preferably has a first thicker area and at least one second thinner area. The containing surface of each portion further has a hole through it. A resilient septum is over-molded within this hole.

When assembled, the two portions are brought together so that surfaces of the two rims are in face-to-face registration. The rims of the two portions are then bonded together ultrasonically or using a suitable adhesive to create a seal so that the contents of the chamber are only accessible through the septum of one of the two portions.

The container arrangement of the present invention is advantageous because it has an interchangeable top or bottom. The chemical can be extracted through either septum using an extraction needle of an extraction station. Further, the shell can have a geometry similar to that of a hockey puck, with each septum at the center, so it has no front or back or top or bottom. Thus, the extraction station can be easily designed to receive the shell so that a septum is automatically aligned with the extraction needle. The thinner areas of the shell prevent gases from building up within the shell because such gasses can permeate in a controlled fashion through these thinner areas. Further, the ratio between the volume and the surface area of the chamber is such that the rate of decomposition of the chemical or the plastic is reduced as compared to prior art sterilant packages. The result is a container highly suited to meet the objectives of the present invention.

The shell described above can be combined with additional packaging elements. For example, a pouch containing the chemical to be stored can be placed within the chamber of the shell. The pouch is preferably impermeable to the chemical stored, but permeable to any gases formed as a result of decomposition of the chemical or the like. Labels can be applied to the shell. Such labels preferably provide information related to the contents of the shell, "use by" date information, safety information and directions for use. Such labels may also include a material that reacts with the chemical stored in the shell to signify the existence of a leak or that the shell and its contents have already been used.

The shell can be placed in a box for shipping and handling. The box can be made of a material that will absorb any of the chemical that might leak from the shell. The shell or the box can also be wrapped or bagged in plastic.

DETAILED DESCRIPTION

Figure 1:
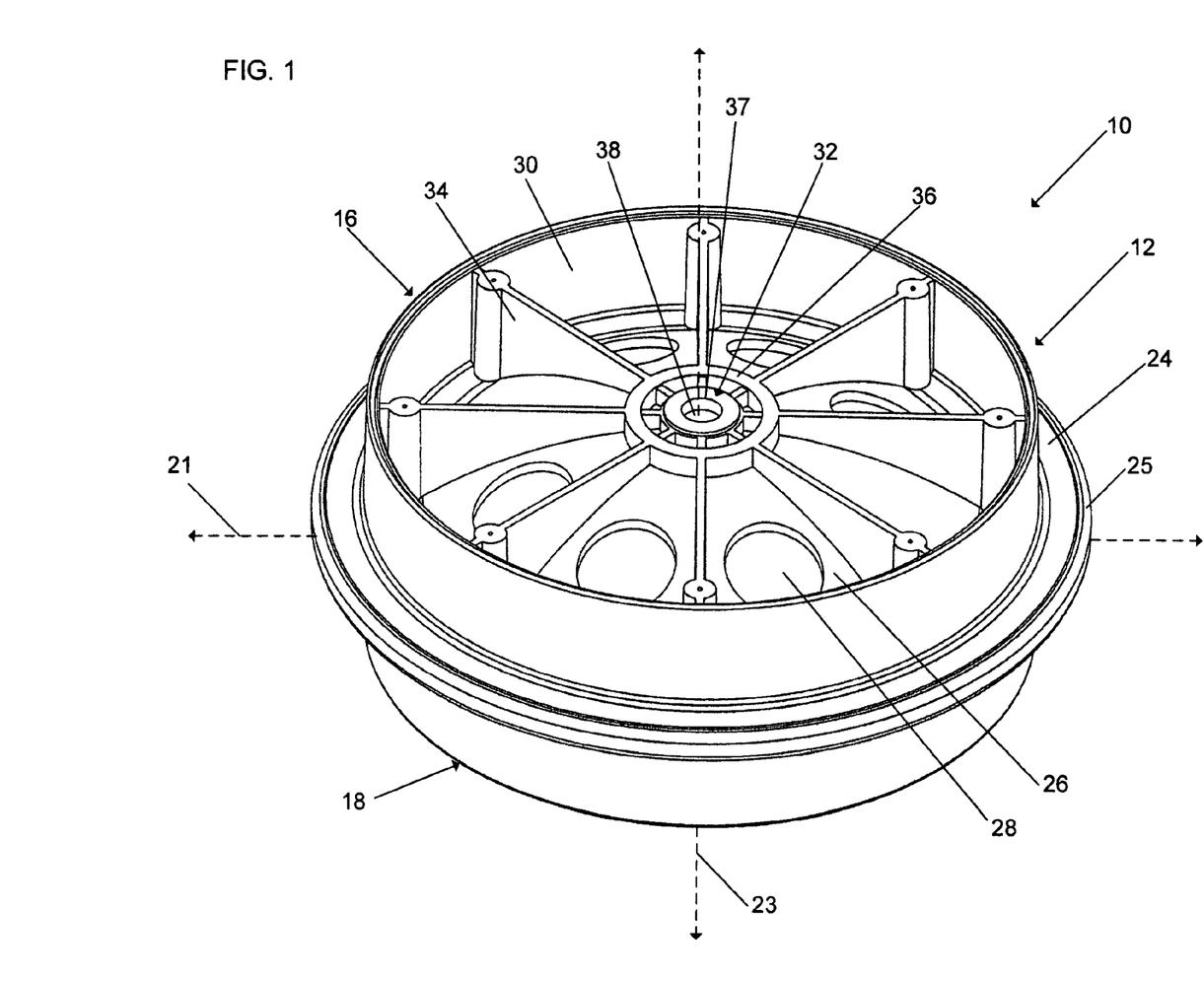
FIG. 1 illustrates a sealed shell with first and second areas of thickness and support features.
Figure 2:
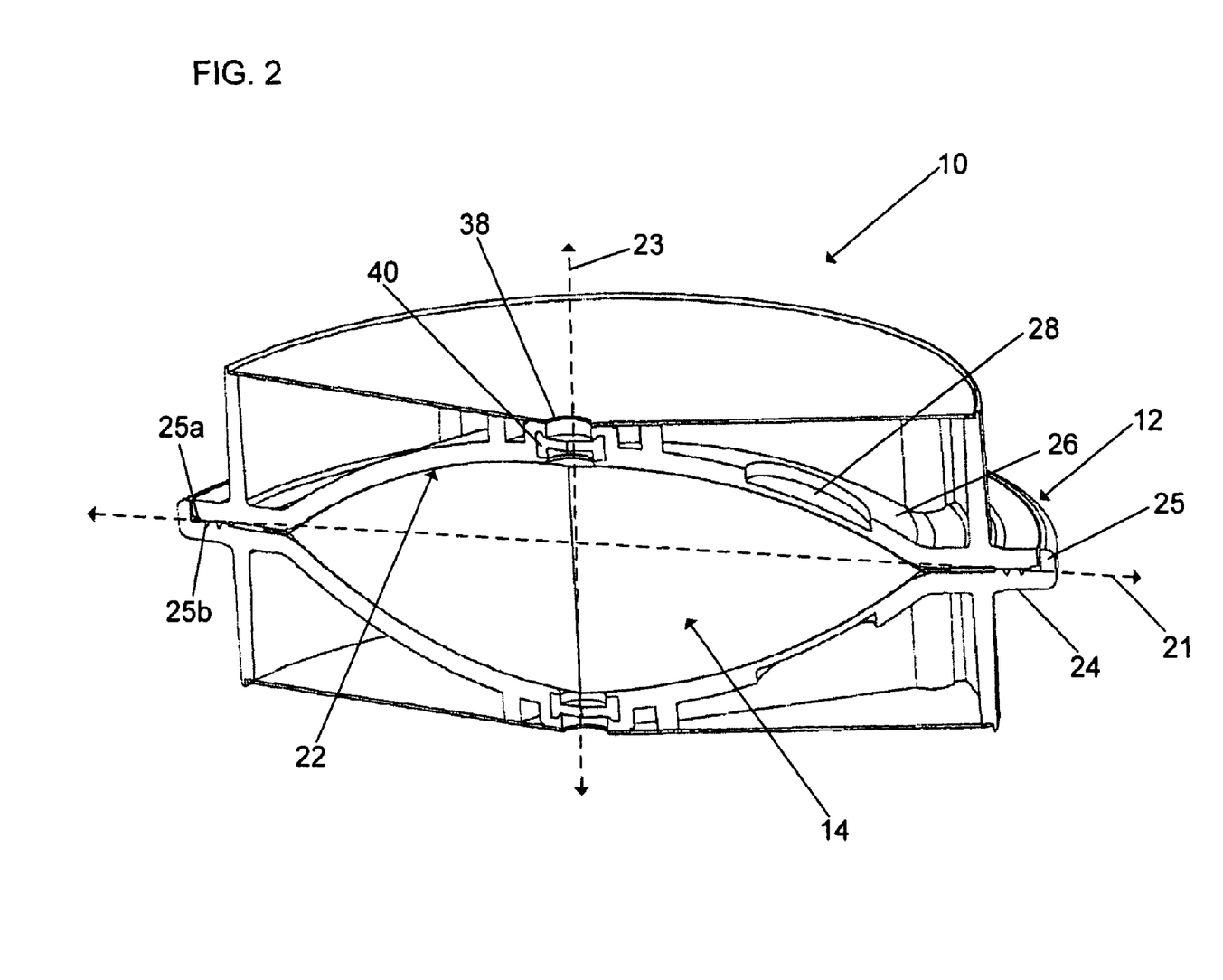
FIG. 2 illustrates a cross-section of the shell.
Figure 3:
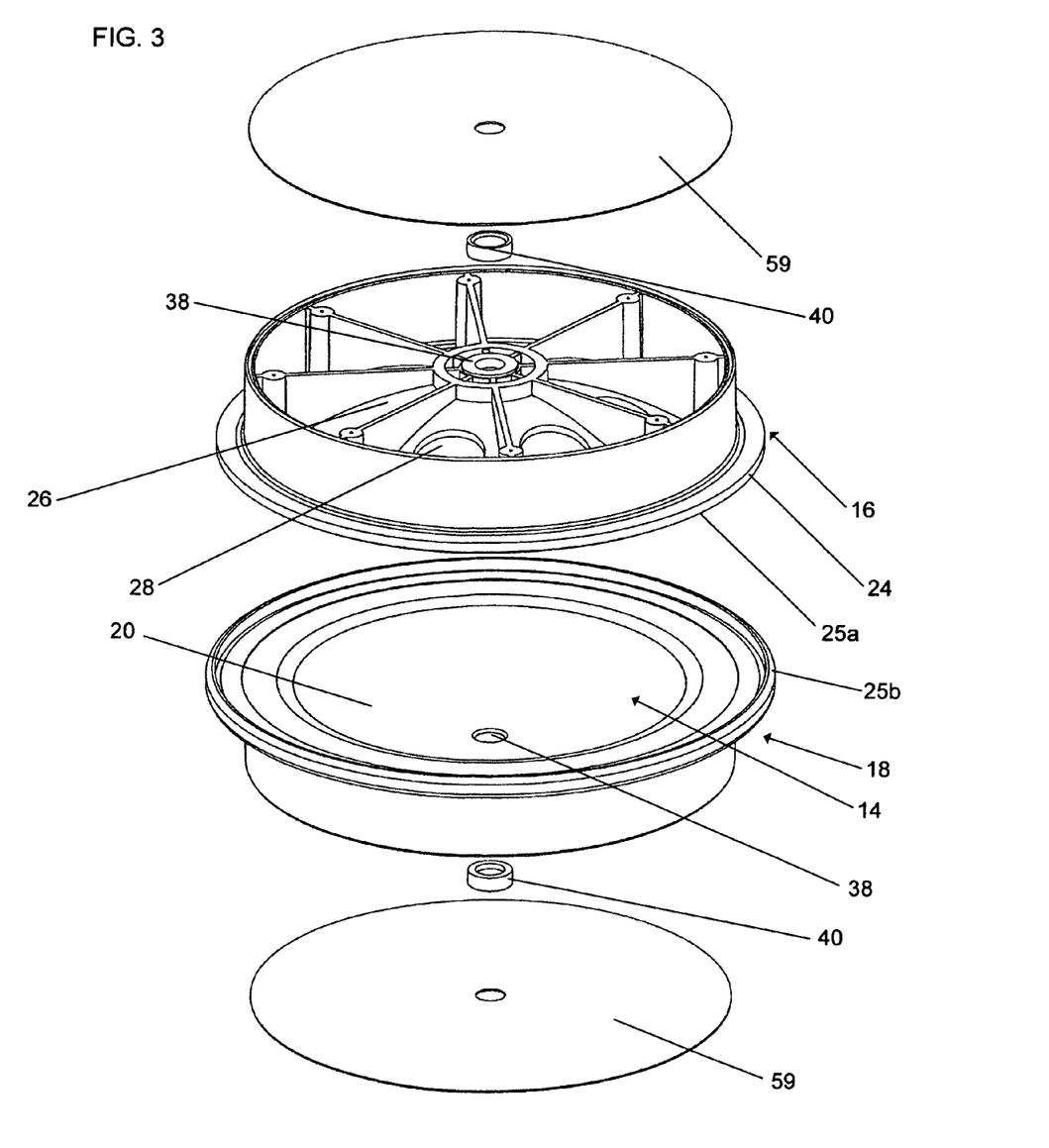
FIG. 3 illustrates an exploded view of the shell.

FIGS. 1-3 show a first embodiment of a container 10 for containing a predetermined chemical compound or mixture which expels at least one gas that is generally not poisonous. The container 10 comprises a shell 12 which defines, surrounds and encapsulates a containment chamber 14 in which a chemical to be stored by container 10 is placed. The shell 12 has a first portion 16 and a second portion 18. As shown, shell portions 16 and 18 are each integrally formed and have a substantially similar structure. Specifically, each shell portion 16 and 18 includes a containing surface 20. The containing surface 20 has a concave shape 22 which terminates in an outwardly projecting rim 24.

The chemical contained in chamber 14 can be virtually any compound or mixture. As is well known in the art, not all compounds and mixtures are stable. Many degrade over time. When this occurs, gases are often generated. It is advantageous to control the accumulation of such gases, more particularly non-toxic gases, from a containment vessel to avoid pressure buildup within the vessel. The shell 12 of the present invention provides this function in a unique fashion.

The material from which the first and second portions 16 and 18 are formed should be substantially impermeable to the stored chemical and to any hazardous gases which may form in the chamber 14 as a result of decomposition of the chemical or the like. However, when the present invention is employed, the material from which at least one of the first and second portions 16 and 18 are constructed should permit permeation of non-hazardous gases that might form in the chamber 14.

Further, the containing surface 20 of at least one of the shell portions 16 and 18 preferably has a first thicker area 26 and one or more second thinner areas 28. Provision of the first and second areas 26 and 28 permit controlled permeation of gases generated by the chemical stored in the chamber 14 through the containing surfaces 20. Such permeation can be controlled not only by material selection, but also by altering the size and number of the second areas 26 and by altering the relative thickness of the first and second areas 26 and 28.

As shown in FIGS. 1-3, each shell portion 16 and 18 further includes various structures to strengthen and support the containing surface 20 and hence the shell 12. These structures include an outer wall 30 at the edge of the containing surface 20 projecting outwardly in a generally perpendicular direction to the outer rim 24. These structures further include a central hub 32 at the center of the convex containing surface 20 and a plurality of gussets 34 extending between the outer wall 30 and the central hub 32. One or more circular intermediate supports 36 may also be provided between the outer wall 30 and the hub 32.

Formed through the center of hub 32 and the containing surface 20 of each of shell portions 16 and 18 is a central opening 38. The central opening 38 is defined by an orifice wall 37. Either central opening 38 can be used to fill the containment chamber 14 with the chemical to be stored in container 10. Likewise, either central opening 38 can be used to extract the chemical from the containment chamber 14. Each of the central openings 38 is sealed by a resilient septum 40. The septum 40 is sized to effectively seal a central opening 38 against the orifice wall 37.

Figure 4:
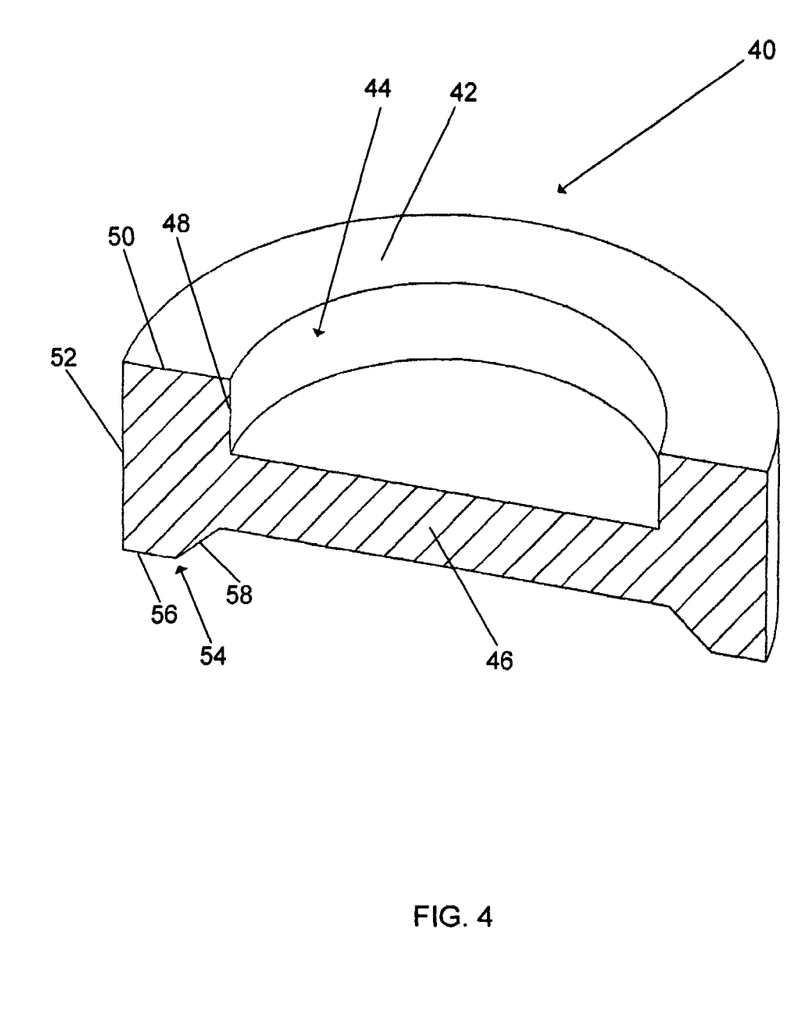
FIG. 4 illustrates a cross-section of the resilient self-sealing septum.
Figure 9:
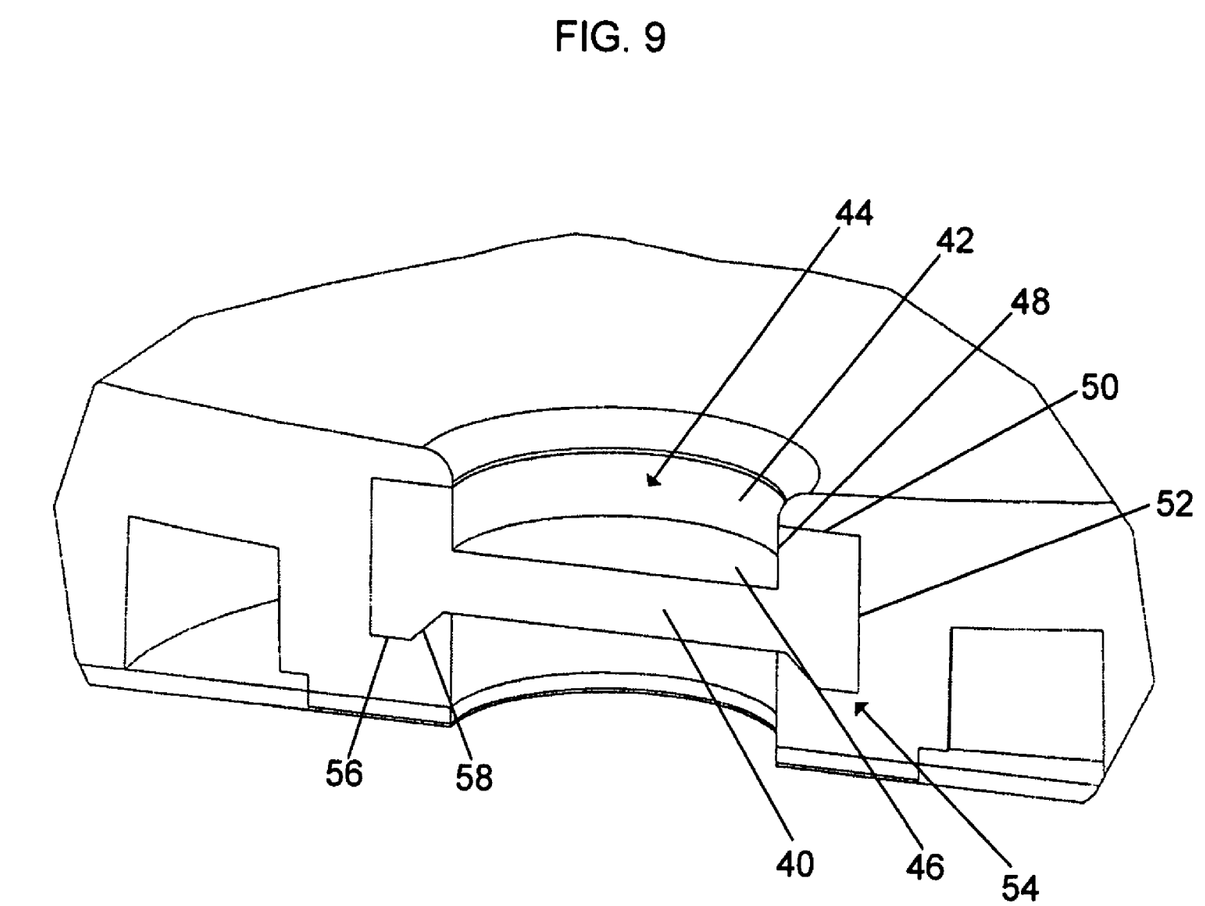
FIG. 9 illustrates a cross-section of the shell and the manner in which it is overmolded with respect to the septum.

FIGS. 4 and 9 show a preferred septum 40. As shown, the septum 40 includes an outer section 42 that is cylindrical in shape that defines a channel 44. Extending across and closing the channel 44 is a center section (or membrane) 46. The entire septum is preferably integrally formed of a material that permits entry of a needle-type probe through the membrane 46 and that will self-close and self-seal upon extraction of such a probe.

The design of the outer section 42 provides important advantages. As shown, the outer section has a first surface 48 that defines the center channel 44. Extending outwardly from the first surface 48 at approximately a 90° angle is a second surface 50. The second surface 50 defines the inner end of the self-sealing septum 40. Extending from the opposite end of the second surface in a direction generally parallel to the first surface 48 and perpendicular to the second surface 50 is a third surface 52. The third surface 52 defines the outside wall of the self-sealing septum 40. A fourth angled surface 54 having two portions 56 and 58 defines the outer end of the self-sealing septum 40. The fourth surface extends from the third surface 52 back toward the first surface 48. While portion 56 of the fourth surface 54 extends in a generally perpendicular direction from the third surface 52, portion 58 of the fourth surface extends at an angle preferably less than 180° and greater than 90° from the portion 56. The angle between the orifice wall 37 and one of the portions of the fourth angled surface of the septum 58 as formed by the overmolding process creates an acute angle and thus provides increased and enhanced sealing between the septum 40 and the shell 12 as pressure increases within the chamber 14. The vertex of this angle can have a small flat portion to prevent cutting of the septum.

As best shown in FIGS. 1 and 2, the container 10 is completed by joining the first and second portions 16 and 18 of the shell 12. To assist in aligning the first and second portions 16 and 18, the rim 24 of the second portion 18 is provided with a lip 25. The inside diameter of the lip 25 is just slightly larger than the outside diameter of the outer rim 24 of the first portion 16. This arrangement allows a first face 25a on the outer rim 24 of the first portion 16 to be easily and securely aligned in face-to-face registration with a second face 25b on the outer rim 24 of the second portion 18. Once so aligned, the first and second portions 16 and 18 are joined together at the outer rims to create a complete seal between the respective first and second portions 16 and 18. This seal may be created using any suitable mechanical means. For example, this seal can be created by ultrasonically welding the outer rims together or by using another suitable adhesive. Other methods or structures for joining and creating a seal between the two outer rims 24 can also be employed without deviating from the invention.

Material selection for each of the first and second portions 16 and 18 of the shell 12, each septum 40 and any adhesive used will be dependent on the characteristics of the chemical to be contained in the chamber 14 and any chemicals generated by decomposition of the chemical or the like. Typically, the first and second portions 16 and 18 of the shell 12 are formed from a thermoplastic or thermoset polymeric material. Other materials could also be employed, such as aluminum. Both the first and second portions 16 and 18 can be formed of the same material. Alternatively, different materials may be used for the first and second portions 16 and 18.

Any material used to construct the shell 12 should be substantially inert to the chemical to be contained in the chamber 14 to prevent failure of the shell 12 and to prevent contamination of the chemical stored. Likewise, the shell material should be of a type that will not significantly catalyze decomposition of the chemical stored. The shell material should also not interact with any gas likely to be generated within the chamber 14 in a way that will lead to failure of the shell 12. As discussed above, however, the material used for at least one of the first and second portions 16 and 18 may be somewhat permeable to any non-toxic gases generated within the shell 12 so that such gases can permeate through the shell 12 in a controlled fashion. The selected shell material should be of a type that can be formed into the shell 12 so it will withstand forces encountered during filling, storing, shipping and use in even the most extreme-environments.

If in direct contact with the material being contained, the septum 40 should likewise be formed from a material that will not interact in an adverse fashion with chemicals to be stored within the chamber 14 or any other chemicals likely to result from decomposition of the stored chemicals.

The embodiment shown in FIGS. 1-3 is ideally suited for use in storing a chemical compound or mixture such as a sterilant. An example of one such sterilant is hydrogen peroxide. When hydrogen peroxide is to be stored in the container 10, a suitable material for use in constructing the shell 12 is acrylonitrile-butadiene-styrene (ABS). ABS is impermeable to liquid hydrogen peroxide, but is somewhat permeable to oxygen. Thus, by controlling the thickness and size of the first areas 26 and second areas 28 of the shell 12 and the number of second areas 28, the degree to which such permeation of oxygen occurs can be controlled.

Various silicone and other materials are suitable for use in constructing each septum 40 when hydrogen peroxide is to be stored. These materials are not adversely affected by hydrogen peroxide or by either water vapor or oxygen which results from decomposition of the hydrogen peroxide. These materials also allow for a self sealing system of the type described to be formed.

Important advantages of the embodiment of FIGS. 1-3 result from the symmetry of the shell 12. Those skilled in the art will recognize that the design is symmetrical along a first axis (or plane) 21 extending between the first and second portions 16 and 18 of the shell 12. Thus, the shell 12 has no predefined top or bottom. Likewise, the shell 12 is symmetrical along a second axis (or plane) 23 extending perpendicular to the first axis and through the center of each of the first and second portions 16 and 18 of the shell 12. Thus, the shell 12 has no established front, back, right or left. This symmetry is achieved in the preferred embodiment because the first and second portions 16 and 18 are substantially circular in shape in a plan view. Such symmetry can be accomplished using other shapes as well.

This symmetry along the two axes 21 and 23 makes it easier to fill the chamber 14 or extract the chemical from the chamber 14 using a needle-type probe of a filling or removal station. The shell 12 can be placed in the filling or removal station with either the first or second portion 16 and 18 facing in an upward direction since the needle-type probe can be inserted through the septum 40 disposed on either the first or second portions 16 and 18 or both portions. Alignment of the probe with the central opening 38 of either the first or second portion 16 and 18 is made by virtue of the symmetry that exists along the second central axis 23.

As shown in FIGS. 2 and 3, a label 59 can be applied to one or both of the first and second portions 16 and 18. The label 59 can provide useful information to the user indicating the contents of the container 10, a packaged-date, a use-by date, safety precautions or the like. The label 59 can also provide other useful information if it is made from or treated with a material that interacts with the chemical stored in the shell 12. For example, if the chemical to be stored in the container 10 is hydrogen peroxide and the label 59 is made from or treated with a material that changes color when exposed to hydrogen peroxide, then the label 59 can provide an indication of whether the contents of the chamber 14 have been extracted or whether the shell 12 has leaked some or all of its contents. Such a label 59 can be secured to the shell 12 using any suitable adhesive or an ultrasonic weld.

Figure 5:
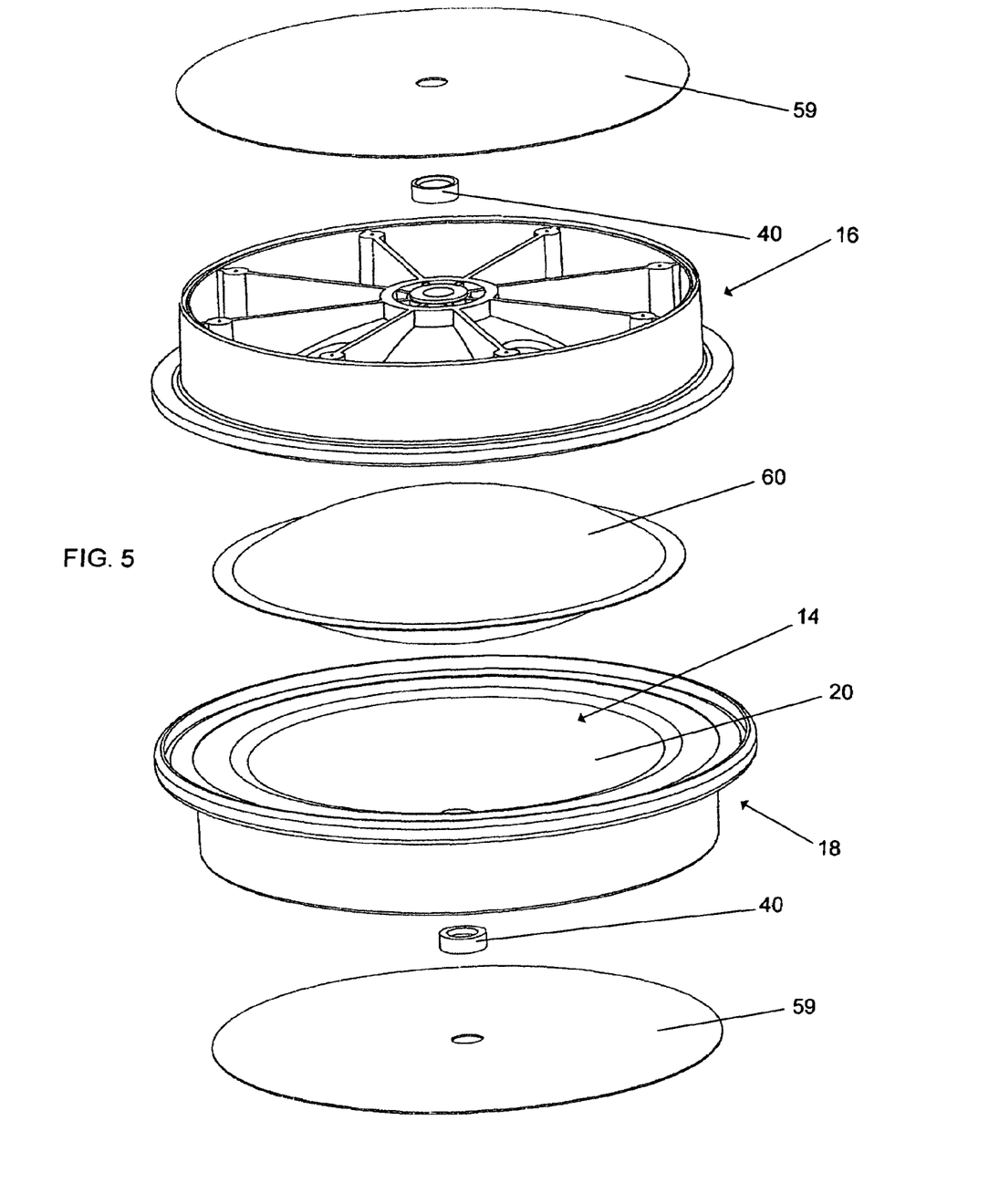
FIG. 5 illustrates an exploded view of the shell containing an inner liner.
Figure 6:
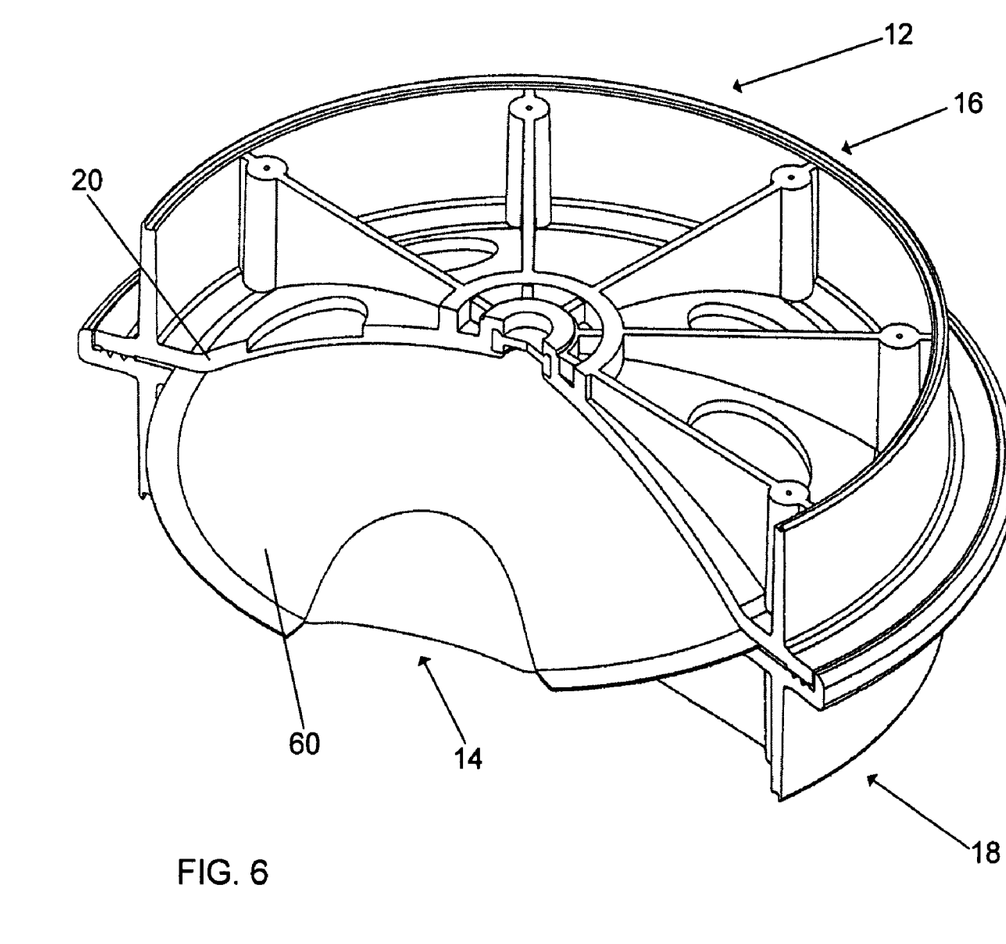
FIG. 6 illustrates a cross-section of the shell containing an inner liner.

FIGS. 5 and 6 show a first alternative embodiment. This embodiment is particularly useful when there is no readily available material for the shell 12 that is both inert to the chemical stored and meets the other shell material requirements outlined above. In this embodiment, a protective liner 60 is bonded to the inside of the containing surface 20 of each the first and second portions 16 and 18 of the shell 12 to form a protective barrier between the shell 12 and the chamber 14. The liner 60 is bonded or attached to the containing surface 20 such that the entire inside portion of containing surface 20, otherwise exposed to the stored chemical, is covered by the liner 60. As such, the liner 60 minimizes the likelihood that the chemical contained within the chamber 14 will contaminate or be contaminated by the material from which the shell 12 is constructed. The liner 60 should be substantially inert to the chemical contained within the chamber 14 and any by-product which may be created from the chemical due to decomposition or the like. Further, the liner 60 should be made from a material which is impermeable to the chemical stored and any hazardous by-products, but permeable to non-toxic gas which may be formed as the chemical degrades. A liner 60 constructed from such a material minimizes the likelihood that the contents of the chamber 14 will leak out of the shell 12 while at the same time permitting one or more non-toxic gases to permeate through the shell 12 and liner 60 thus reducing pressure in the container 10.

Figure 7:
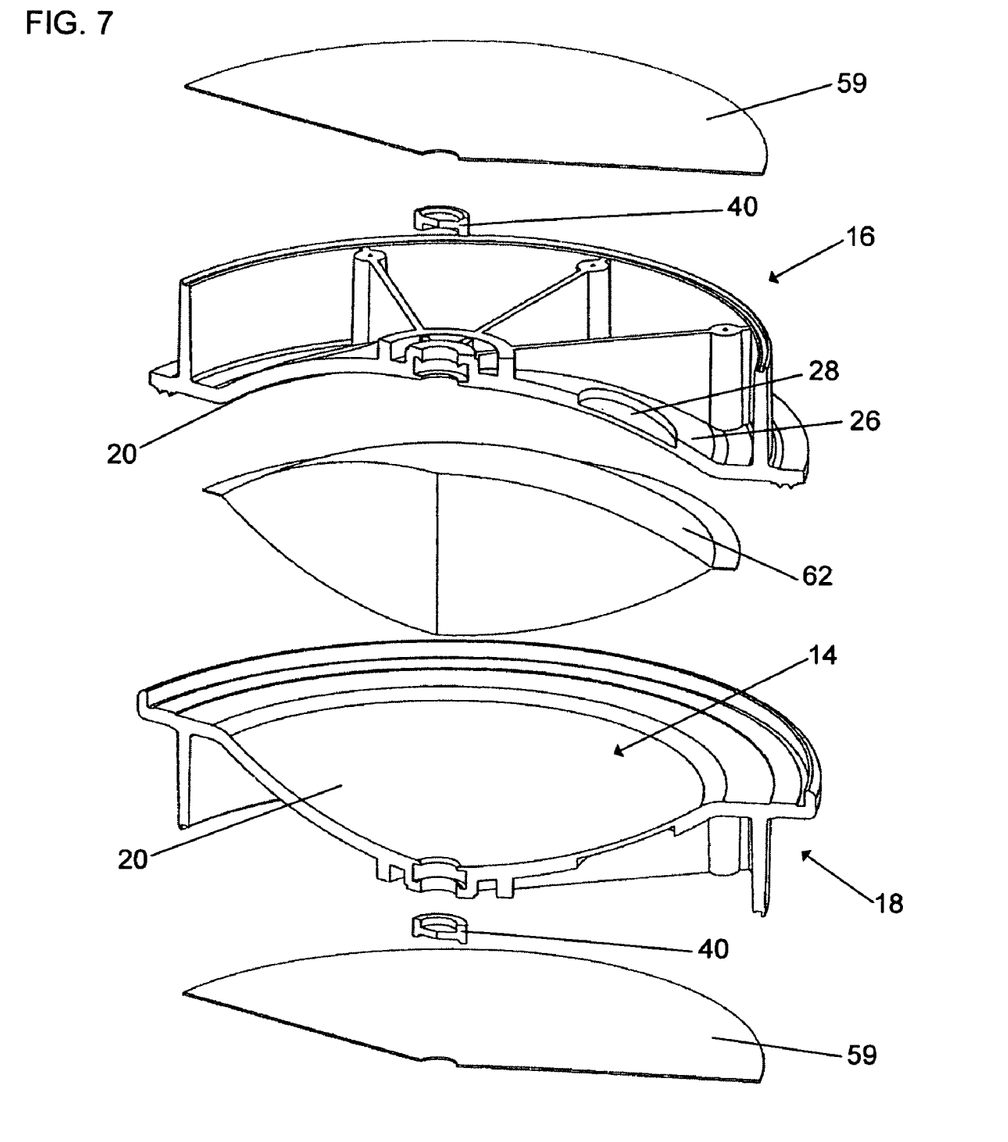
FIG. 7 illustrates an exploded cross-section of the shell containing a pouch.

FIG. 7 shows another alternative embodiment. In this embodiment, a pouch 62 is employed. Specifically, the pouch 62 is disposed within the chamber 14 either in place of or in addition to the inner liner 60. The chemical to be stored in the container is sealed within the pouch 62 and the pouch 62 is disposed, contained and sealed within the chamber 14. Like the liner 60, the pouch 62 is preferably impermeable to the chemical which it contains as well as any hazardous by-products, but permeable to the non-toxic gas which may be released from the chemical as the chemical degrades. The material of the pouch 62 should be substantially inert with respect to the chemical stored in the pouch 62 or any by-products formed by decomposition of the chemical to prevent contamination of the chemical and decomposition of the pouch 62. The pouch 62 should further be formed to substantially conform to the shape of the chamber 14 so as to maximize the pouch-volume/chamber-volume ratio.

The material selected for the inner liner 60 and the pouch 62 will depend on the characteristics of the chemical to be contained within the inner liner 60 or the pouch 62 and any by-products generated by decomposition of the contained chemical or the like. Typically, the inner liner 60 and the pouch 62 are constructed from a polymeric material. The polymeric material selected must conform with the requirements previously stated regarding the material being substantially inert to the contained chemical and being permeable to non-toxic gases released from the decomposition of the chemical.

The inner liner 60 and the pouch 62 as described above and as shown in FIGS. 5-7 are ideally suited for use in storing a chemical such as a sterilant. When the chemical contained in the chamber is a sterilant such as hydrogen peroxide, suitable materials for use in constructing the inner liner 60 or the pouch 62 include: fluorinated-ethylene-propylene (FEP), polyethylene, perfluoroalkoxy (PFA), and polytetrafluoroethylene (PTFE). Other materials known in the art which are also substantially inert to hydrogen peroxide, oxygen and water vapor and which allow the permeation of oxygen may also be used.

Figure 8:
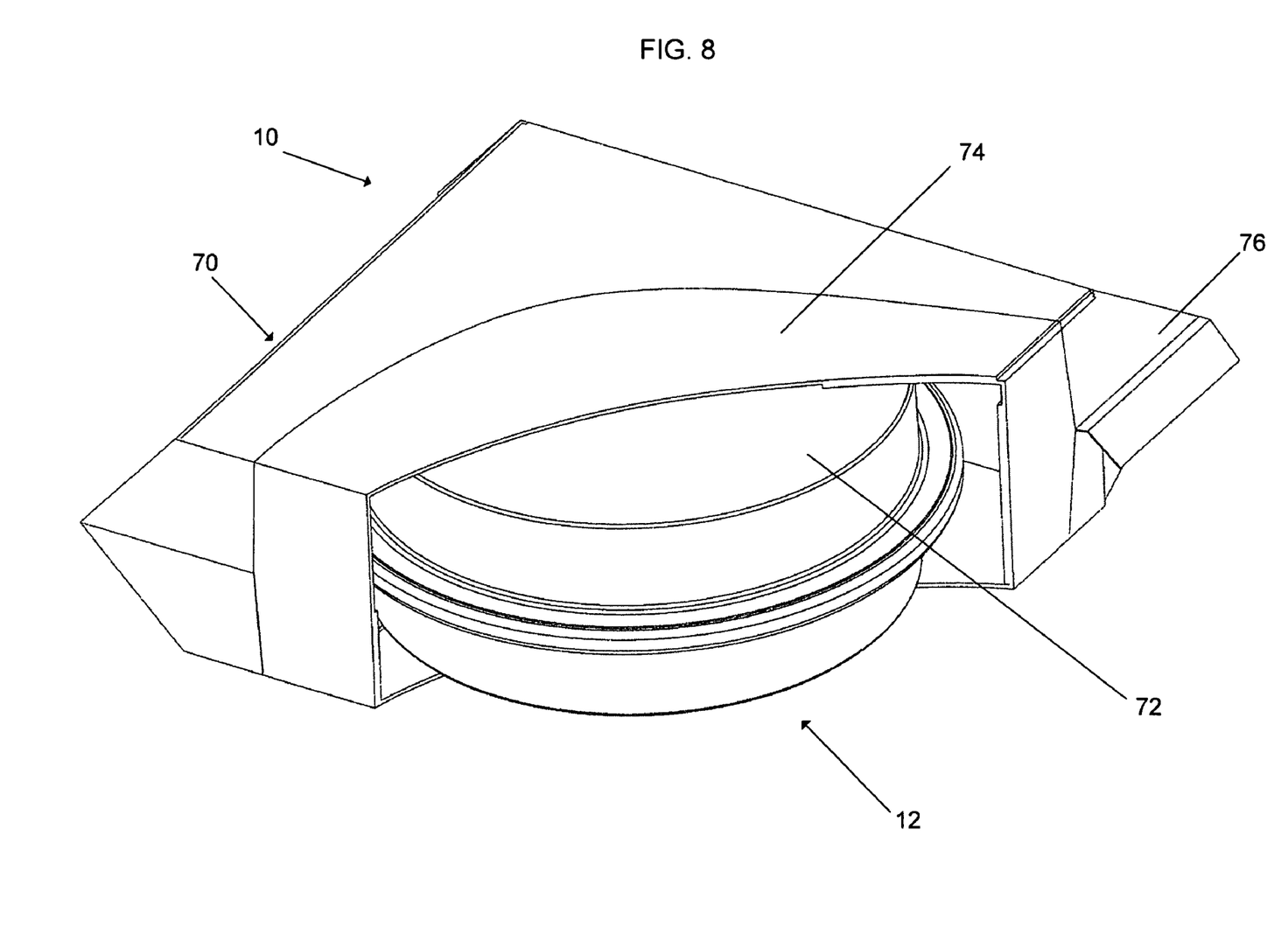
FIG. 8 illustrates the container comprising an outer casing and the shell.

FIG. 8 represents still another embodiment of the present invention. The embodiment of FIG. 8 includes the shell 12 with or without the liner 60 or pouch 62. The embodiment of FIG. 8 further includes an outer package, i.e. casing 70, surrounding and encapsulating the shell 12. As shown, the outer casing, 70 has three layers, an absorbent layer 72, a cushioning layer 74 and a liquid-tight layer 76. The absorbent layer 72 is ideally disposed adjacent to the shell 12 but may be located at any position within the liquid-tight layer 76. The function of the absorbent layer 72 is to absorb substantially all of the chemical contained within the chamber 14 in the event the shell 12 leaks. The absorbent layer 72 could also be made of a material that acts as an indicator in the event of such a leak. For example, the material of absorbent layer 72 could change color or provide another means of indication when it comes into contact with the chemical stored in the chamber 14.

The cushioning layer 74 is provided to cushion the shell 12 from the forces that could be encountered during use, storage and transportation. This cushioning layer 74 could be constructed from cardboard, bubble wrap or any of a variety of other suitable materials of sufficient thickness to protect the shell 12 from external forces. An indicator could appear on the surface of the cushioning layer 74 or as a sticker attached to any surface visible to the user to inform the user of a leak.

The liquid-tight layer 76 should completely surround and encapsulate the shell 12 and preferably the absorbent layer 72. The liquid-tight layer 76 can also encapsulate the cushioning layer 74. The liquid-tight layer 76 should be constructed from a material which is generally transparent so the user will be able to see if any of the chemical has been released from the chamber 14. If the liquid-tight layer 76 is not transparent, an indication means may be employed to allow a user to observe if any chemical contained in the chamber has been released.

Since the liquid-tight layer 76 serves as a final layer of protection, it should be impermeable to the chemical contained within the chamber 14, substantially inert to the chemical contained within the chamber 14 as well as any gases which are expelled from the chemical due to decomposition or the like.

From the foregoing, those skilled in the art will understand that the material selected for the various layers of the outer casing 70 will be dependent upon the characteristics of the chemical contained within the chamber 14 and any of the by-products generated. Those skilled in the art will further recognize that the three primary functions described above provided by the outer casing 70 may be provided that has less than three layers. For example, the cushioning layer 74 could be sufficiently absorbent to absorb all of the chemical contained within the chamber 14 in the event of leakage and at the same time provide an indication that a leak has occurred. Likewise, there may be a material suitable for use in constructing the outer casing 70 that provides all three of the preferred functions. Further, even when three layers are employed, it is not necessary that they be arranged as shown in FIG. 8. The liquid-tight layer 76 could be, for example, inside of the cushioning layer 74 instead of outside of the cushioning layer 74 as shown.

The various embodiments shown in the accompanying drawings and described above have been presented to meet the disclosure requirements of the patent laws. The discussion and drawings are not intended to be limiting and those of ordinary skill in the art will appreciate that various alternative embodiments can be employed without deviating from the invention. For example, it is not entirely necessary that the shell 12 be circular in plan view. The shell could be constructed in the shape of a triangle, square, rectangle or any other polygon. Preferably, however, the shell 12 will be symmetrical along at least one axis and preferably two axes. Likewise, the arrangement of the gussets 34 and other support structures 30, 32 and 36 can easily be modified from what is shown in the drawings without deviating from the invention. Further, while the first portion 16 and second portion 18 of the shell 12 are preferably constructed from the same material and have generally the same configuration, other embodiments could be employed where this is not the case. For example, the first and second portions 16 and 18 of the shell 12 could be constructed of differing materials. For example, one portion may be constructed of aluminum and the other portion may be constructed of a thermoplastic or thermoset material. Further, even when the first and second portions 16 and 18 are constructed from the same material, only one of the two portions may be provided with both first and second areas 26 and 28 to assist in controlling the rate of permeation of gas from the chamber 14. Many materials may be suitable in constructing the shell 12 including metals, alloys, polymers or the like and it is not necessary that all components of the shell 12 be constructed of the same material.

Further, without deviating from the invention, material selection alternatively can be used to regulate permeation of gas through a containing surface 20 of the shell 12, particularly if the first areas 26 are made of a material that is either impermeable to the gas or less permeable than the material from which the second areas 28 are made. In such a case, the containing surface 20 may have a uniform thickness and permeation that is a function of the material selected for the second areas 28. Further control may be achieved by regulating the size and number of second areas 28.

While the embodiments described above contemplate a separate label 59 attached to the shell 12, the labeling information could be printed on the shell 12. Such information could be related to the contents of the shell, directions for use and information related to the date the chemical was packaged or a use-by date. Any information that could be printed on a separate label 59 could be printed on the shell 12 and vice versa. Likewise, a separate indicator could be used to inform the user if the chemical had been released from the chamber 14 either as a result of prior use or as the result of leakage. This indicator would not necessarily be part of a more standard label 59.

When a pouch 62 is employed, the septum 40 may be disposed on the surface of the pouch 62 as opposed to in the shell 12. Alternatively, the septum 40 may be disposed in both the shell 12 and the pouch 62.

As noted above, the septum 40 should ideally be constructed from a material that is self-sealing. Having a self-sealing septum offers numerous advantages. First, it permits a needle probe of the type described above to be used to insert chemical into the chamber through the septum 40. After the chemical has been inserted into the chamber 14, the needle probe can be removed and the septum 40 then seals. Likewise, an extraction probe can be inserted through the septum 40 to withdraw chemical from the interior of the chamber on multiple, separate occasions when a self-sealing septum 40 is used.

Other reasonable variations and modifications of the invention are possible without departing from the spirit and scope of the invention. Such reasonable variations and their equivalents should be deemed a part of this invention which is only limited by the following claims.

What is claimed is:

1. For a chemical compound or mixture that expels at least one gas that is generally not poisonous, a container comprising resilient, self-sealing septa and a shell defining, surrounding and encapsulating a chamber in which said compound or mixture is contained, said shell having first and second portions each integrally formed and comprising (i) an outer rim and (ii) a containing surface, wherein the containing surface of said first portion has at least one first area and at least one second area, said second area being thinner than said first area so that said gas may more readily permeate from said chamber through said second area, wherein each of said first and second portions has an orifice wall surrounding an opening through its containing surface sealed by one of the resilient, self-sealing septa such that said compound or mixture can be withdrawn from said chamber through any of the resilient, self-sealing septa, and wherein said containing surface of said second portion further comprises at least one first area and at least one second area, said second area being thinner than said first area so that gas may more readily permeate from said chamber through said second area.

2. The container of claim 1 wherein each of said first and second portions are each symmetrical along at least one axis.

3. The container of claim 1 wherein each of said first and second portions are each symmetrical along at least two axes.

4. The container of claim 1 wherein each of said first and second portions are substantially circular in shape in a plan view.

5. The container of claim 1 wherein at least one of said first and second portions of said shell is constructed from a thermoplastic material.

6. The container of claim 5 wherein said thermoplastic material is acrylonitrile-butadiene-styrene.

7. The container of claim 1 wherein at least one of said first and second portions of said shell is constructed from a thermoset material.

8. The container of claim 1 wherein both of said first and second portions of said shell are constructed from the same material.

9. The container of claim 1 wherein the containing surface of at least one of said first and second portions comprises an inner liner bonded to a containing surface.

10. The container of claim 1 further comprising a pouch disposed within said chamber.

11. The container of claim 10 wherein said pouch is preformed to substantially conform to the shape of said chamber.

12. The container of claim 10 wherein said pouch contains said compound or mixture.

13. The container of claim 10 wherein said pouch is constructed of a material which is substantially inert to said chemical compound or mixture.

14. The container of claim 1 wherein said chemical compound or mixture is a sterilant.

15. The container of claim 14 wherein said sterilant is hydrogen peroxide.

16. The container of claim 10 wherein said pouch is constructed from a polymeric material.

17. The container of claim 16 wherein said polymeric material is selected from a group of polymeric materials comprising fluorinated-ethylene-propylene, polyethylene, perfluoroalkoxy, or polytetraflouroethene.

18. The container of claim 10 wherein said pouch is constructed from a material that is permeable to said at least one gas and substantially impermeable to said chemical compound or mixture.

19. The container of claim 10 wherein said septum is attached to said pouch.

20. The container of claim 1 wherein said at least one gas comprises oxygen.

21. The container of claim 1 wherein said at least one gas comprises water vapor.

22. The container of claim 1 further comprising at least one label attached to or printed on at least one of said first and second portions.

23. The container of claim 22 wherein said at least one label is joined to at least one said first and second portions by an ultrasonic weld.

24. The container of claim 22 wherein said at least one label is attached to at least one of said first and second portions using an adhesive.

25. The container of claim 1 wherein said rim of said first portion has a first face and said rim of said second portion has a second face and said first and second faces are in face-to-face registration and bonded together to form a seal.

26. The container of claim 25 wherein said seal is formed by a mechanical means.

27. The container of claim 25 wherein said seal is formed by an adhesive.

28. The container of claim 25 wherein said seal is formed by an ultrasonic weld.

29. The container of claim 1 wherein at least one self-sealing septa is constructed from a plastic material.

30. The container of claim 29 wherein said plastic material is a silicone material.

31. The container of claim 1 wherein the geometry of at least one self-sealing septum permits said self-sealing septum to effectively seal against that orifice wall.

32. The container of claim 31 wherein the geometry of that self-sealing septum and the geometry of said orifice wall are such that said seal is enhanced in the event pressure in said chamber increases.

33. The container of claim 1 wherein at least one self-sealing septum is integrally formed and includes an outer section over-molded with said material used to form one of said first and second portions of said shell and a center section that extends from said outer section across said opening to close said opening.

34. The container of claim 33 wherein said outer section further comprises a first surface extending in a generally perpendicular direction from said center section towards said chamber, a second surface extending in a substantially perpendicular direction from said first surface away from said opening, a third surface extending from said second surface away from said chamber and past said center section in a direction generally parallel to the orifice wall, and a fourth surface extending from said third surface back toward said opening and said center section, at least a portion of said fourth surface not being perpendicular to either said third surface or said center section.

35. The container of claim 1 wherein said shell is surrounded by an outer package.

36. The container of claim 35 wherein said outer package comprises a cushioning layer of sufficient thickness to protect said shell from external forces.

37. The container of claim 35 wherein said outer package comprises an absorbent material.

38. The container of claim 37 wherein said absorbent material can absorb substantially all of said chemical compound or mixture contained in said chamber should a leak occur.

39. The container of claim 35 wherein said outer package comprises a liquid-tight layer.

40. The container of claim 39 further comprising an absorbent material disposed between said liquid-tight layer and said shell.

41. The container of claim 39 wherein said liquid-tight layer encapsulates said shell and a cushioning layer.

42. The container of claim 35 wherein said outer package comprises a cushioning layer, an absorbent material, and a liquid-tight layer.

43. The container of claim 1 wherein said shell is surrounded by a liquid-tight enclosure.

44. The container of claim 1 further comprising a chemical indicator label which is activated by said chemical compound or mixture contained in said chamber should a leak occur.

45. The container of claim 1 wherein each of said first and second portions each further comprise a plurality of support gussets.

46. For a chemical compound or mixture that expels at least one gas that is generally not poisonous, a container comprising (a) a shell having first and second portions defining, surrounding and encapsulating a chamber, (b) a first self-sealing septum, and (c) a second self-sealing septum, wherein each of said first and second portions is integrally formed and comprises (i) an outer rim having a face bonded to a face of the rim of the other portion, (ii) a lip projecting from said outer rim in a direction away from the other portion, (iii) a containing surface having at least one first area and at least one second area, said second area being thinner than said first area so that said at least one gas may more readily permeate from the chamber through said second area, (iv) a plurality of support gussets, and (v) an orifice wall surrounding an opening through said containing surface sealed by either said first self-sealing septum or said second self-sealing septum such that said chemical compound or mixture can be withdrawn from said chamber through either said first self-sealing septum or said second self-sealing septum.

\* \* \* \* \*

UNITED STATES PATENT AND TRADEMARK OFFICE
CERTIFICATE OF CORRECTION

PATENT NO.       : 7,993,609 B2
APPLICATION NO.  : 12/317894
DATED            : August 9, 2011
INVENTOR(S)      : Patrick LaValley Page 1 of 1

It is certified that error appears in the above-identified patent and that said Letters Patent is hereby corrected as shown below:

Column 12, claim 31, line 32 should read "permits that self-sealing septum"; line 33 should read "said orifice wall".

Signed and Sealed this
Twenty-seventh Day of September, 2011

David J. Kappos
*Director of the United States Patent and Trademark Office*